(12) United States Patent
White et al.

(10) Patent No.: US 7,819,318 B2
(45) Date of Patent: Oct. 26, 2010

(54) INTELLIGENT IMPLEMENT HAVING METAL ENCASED PASSIVE RADIO FREQUENCY TRANSPONDER AND EXAMPLES OF USE

(75) Inventors: Patrick M. White, West Chester, PA (US); Patrick Berdoz, Chester Springs, PA (US); Philippe Fehlbaum, Lignieres (CH)

(73) Assignee: Greatbatch Medical S.A., Orvin (CH)

( * ) Notice: Subject to any disclaimer, the term of this patent is extended or adjusted under 35 U.S.C. 154(b) by 742 days.

(21) Appl. No.: 11/577,092

(22) PCT Filed: Dec. 15, 2005

(86) PCT No.: PCT/IB2005/003922

§ 371 (c)(1),
(2), (4) Date: Apr. 12, 2007

(87) PCT Pub. No.: WO2006/067610

PCT Pub. Date: Jun. 29, 2006

(65) Prior Publication Data

US 2009/0283595 A1    Nov. 19, 2009

Related U.S. Application Data

(60) Provisional application No. 60/639,235, filed on Dec. 22, 2004, provisional application No. 60/669,953, filed on Apr. 8, 2005.

(51) Int. Cl.
| | |
|---|---|
| *G06F 19/00* | (2006.01) |
| *G06Q 30/00* | (2006.01) |
| *G06Q 90/00* | (2006.01) |
| *G06K 19/06* | (2006.01) |
| *G06K 19/02* | (2006.01) |
| *A61B 17/00* | (2006.01) |
| *A61B 18/04* | (2006.01) |
| *A61B 18/18* | (2006.01) |
| *H01Q 1/24* | (2006.01) |

(52) U.S. Cl. ............ 235/385; 235/492; 235/488; 606/1; 606/33; 606/43; 343/702

(58) Field of Classification Search ........... 235/492, 235/485, 488, 375; 606/130, 39, 41, 1, 33, 606/185; 600/468, 463, 422, 2; 343/702, 343/715

See application file for complete search history.

(56) References Cited

U.S. PATENT DOCUMENTS 3,531,582 A * 9/1970 Walker .............. 235/488

(Continued)

FOREIGN PATENT DOCUMENTS

DE    200 15 893    3/2001

(Continued)

*Primary Examiner*—Thien M. Le
*Assistant Examiner*—Thien T Mai
(74) *Attorney, Agent, or Firm*—Michael F. Scalise

(57) ABSTRACT

A metal-encased passive radio-frequency transponder assembly includes a metal housing having an external surface and an opening accessing an interior space, the opening closeable with a metal cover to provide a solid metal encasement. The interior space of the encasement is defined by the interior walls of the housing and cover. The solid metal encasement has a substantially uniform wall thickness between the interior wall surface adjacent which an antenna assembly is disposed and the opposing external surface of less than about 0.5 mm. A passive radio-frequency transponder device is received within the interior space of the housing. The passive transponder device has an iron core antenna assembly. The antenna assembly is disposed adjacent the interior wall surface of the interior space and oriented to maximally couple a radio-frequency signal present at the interior wall surface to an antenna of the antenna assembly.

13 Claims, 13 Drawing Sheets

U.S. PATENT DOCUMENTS

| | | | |
|---|---|---|---|
| 5,218,187 A * | 6/1993 | Koenck et al. | 235/375 |
| 5,405,346 A * | 4/1995 | Grundy et al. | 606/41 |
| 5,598,032 A * | 1/1997 | Fidalgo | 235/492 |
| 5,787,886 A * | 8/1998 | Kelly et al. | 606/130 |
| 5,800,378 A * | 9/1998 | Edwards et al. | 606/39 |
| 6,176,425 B1 * | 1/2001 | Harrison et al. | 235/385 |
| 6,233,490 B1 * | 5/2001 | Kasevich | 606/33 |
| 6,254,389 B1 * | 7/2001 | Seghatol | 606/41 |
| 6,277,113 B1 * | 8/2001 | Berube | 606/33 |
| 6,503,191 B1 * | 1/2003 | Miller | 606/33 |
| 6,746,464 B1 * | 6/2004 | Makower | 606/185 |

FOREIGN PATENT DOCUMENTS

| | | |
|---|---|---|
| DE | 100 14 542 | 10/2001 |
| DE | 102 39 710 | 3/2004 |
| EP | 1 308 883 | 5/2003 |
| WO | WO 2004/042677 | 5/2004 |

* cited by examiner

GLASS TAG
Unique - 2.12 x 12.0

| | | | Test conditions and remarks |
|---|---|---|---|
| Chip type: | UNIQUE - read only 64 bits | | |
| Physical: | Diameter. | 2,12 mm ± 0.1 mm | |
| | Length. | 12.0 mm ± 0.4 mm | |
| | Weight. | 95mg | |
| | Material. | BIO GLASS 8625 | |
| | Color. | Transparent | |
| Electrical: | Operating frequency | 125 kHz ± 6 kHz | At room temperature |
| Chemical: | Water immersion IP68 | | 20°C, 24h 1m |
| | Aqueous solution of salts | | 20°C, 100h |
| | Alcohol. oil. HLC (10% | | 20°C, 100h |
| | Ammoniac | | 20°C, 100h |
| Mechanical | Vibration | ICE 68.3.6 | 6g 14...200Hz, 3 axis, 8tv/axis |
| | Schock | ICE 68.2.29 | 30g 18ms, 3 axis, 1084 times/axis |
| Thermal: | Storage. | -40°C to + 90°C | 1 X1000h |
| | | +120°C | 1 X100h |
| | Operating | -40°C to + 85°C | |
| Part number: | 601201 | | |

FIG. 6A

| | GLASS TAG |  |  |
|---|---|---|---|
| | Unique - 3.15 x 13.3 | | |
| Chip type: | UNIQUE - read only 64 bits | | Test conditions and remarks |
| Physical: | Diameter. | 2,12 mm ± 0.1 mm | |
| | Length. | 12.0 mm ± 0.4 mm | |
| | Weight. | 95mg | |
| | Material. | BIO GLASS 8625 | |
| | Color. | Transparent | |
| Electrical: | Operating frequency | 125 kHz ± 6 kHz | At room temperature |
| Chemical: | Water immersion IP68 | | $20^0$C, 24h 1m |
| | Aqueous solution of salts | | $20^0$C, 100h |
| | Alcohol. oil. HLC (10%) | | $20^0$C, 100h |
| | Ammoniac | | $20^0$C, 100h |
| Mechanical: | Axial compression | 500 N | 10s |
| | Radial comprerssion | 500 N | 10s |
| | Vibration | ICE 68.2.6 | 6g 14...200Hz, 3 axis, 8tv/axis |
| | Schock | ICE 68.2.27 | 30g 18ms, 3 axis, 1084 times/axis |
| Thermal: | Storage. | $-40^0$C to $+90^0$C | 1 X1000h |
| | | $+120^0$C | |
| | Operating | $-40^0$C to $+85^0$C | 1 X100h |
| Part number: | 601203 | | |

FIG. 6B

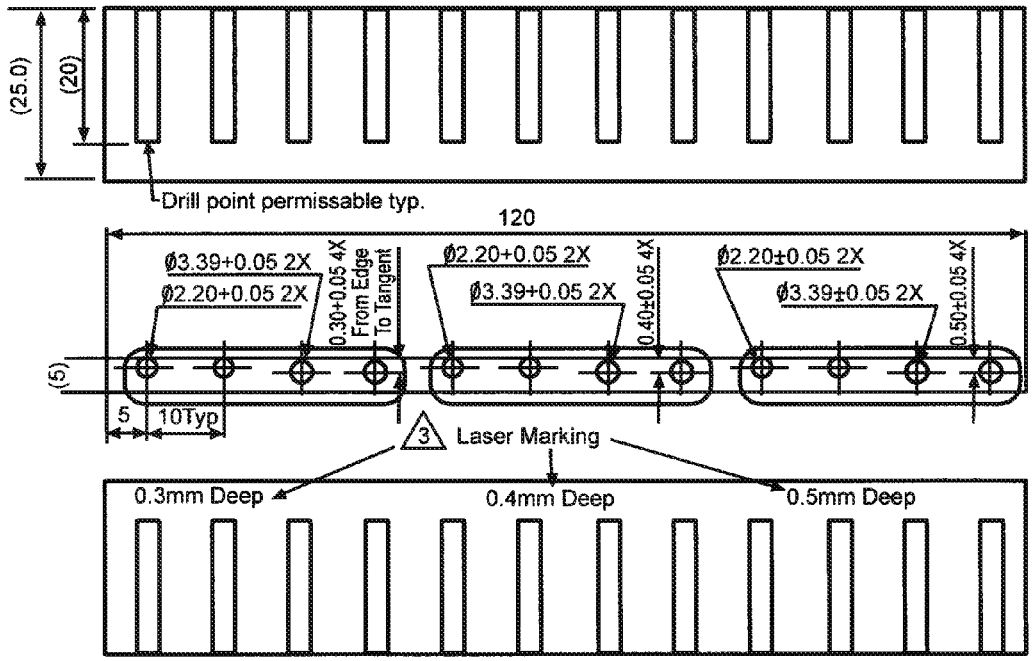
Notes:
1. Ø2.2 mm Hole for small RFO.
2. Ø3.25mm Hole for Large PFD.
3. Laser marks as shown in bottom view.
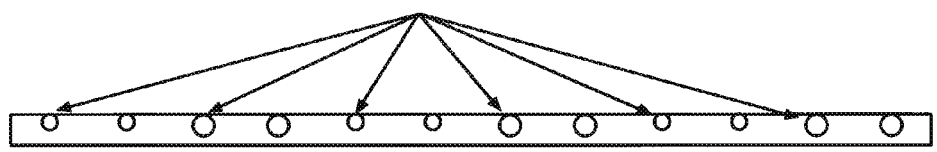
Insert Approprate RDO Plug With
17.4 PH Plug and Lassr Weld
6 Holes shown.
FIG. 6C

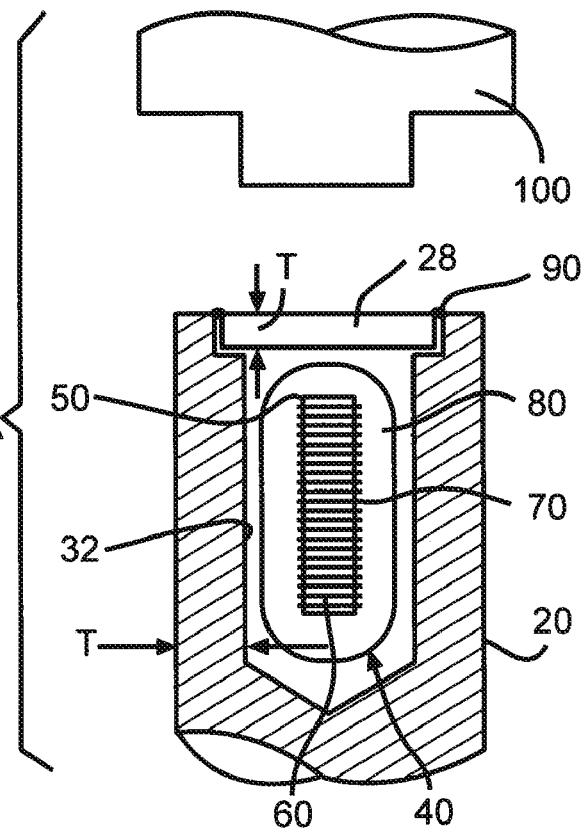
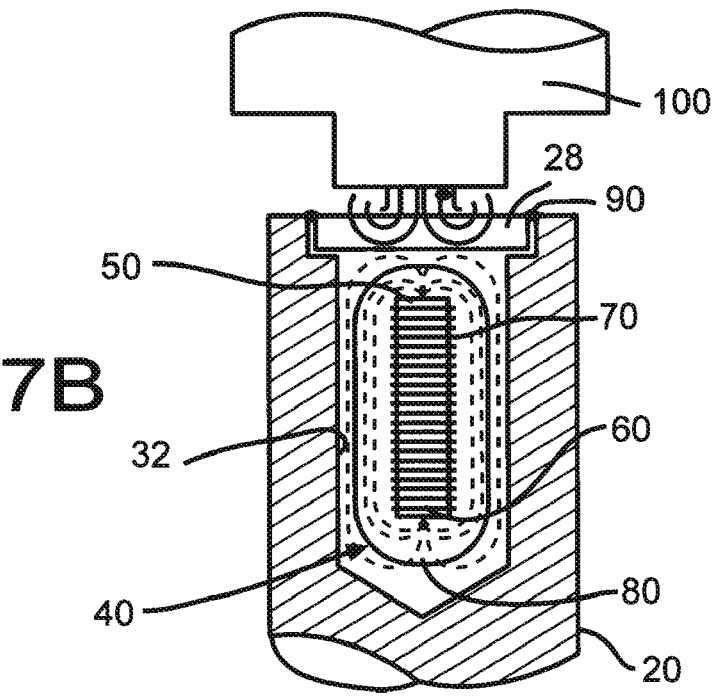

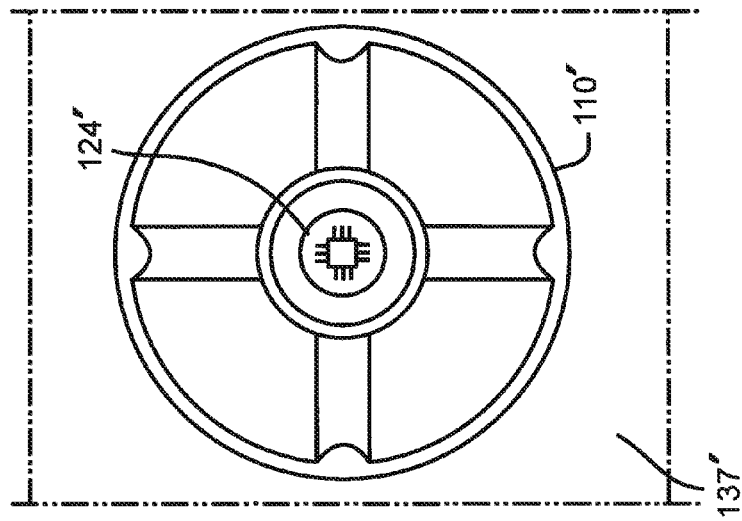
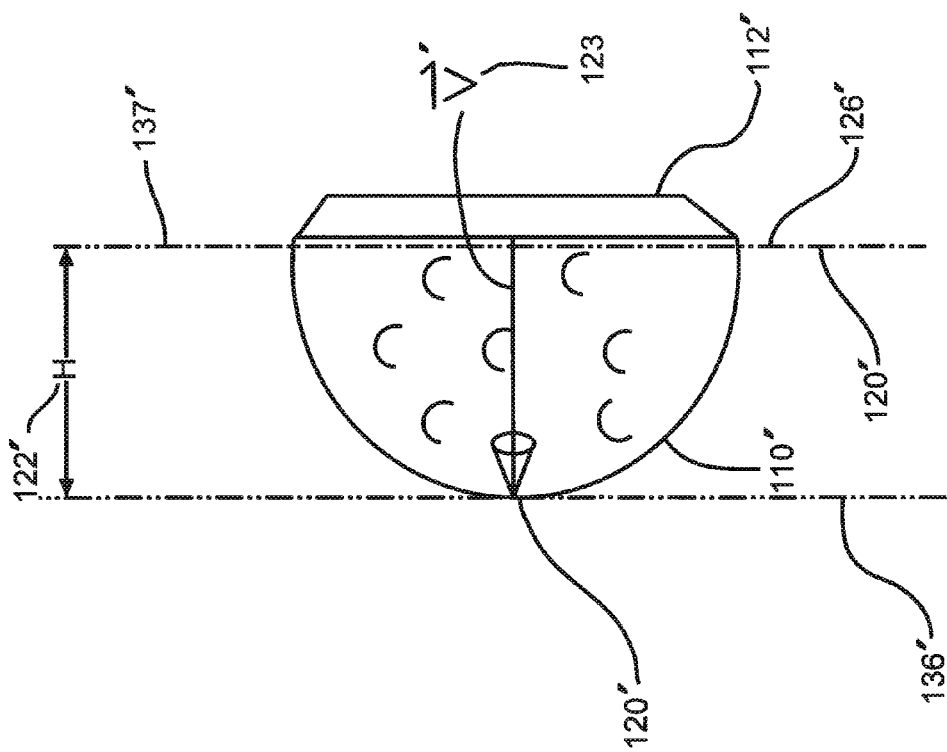

INTELLIGENT IMPLEMENT HAVING METAL ENCASED PASSIVE RADIO FREQUENCY TRANSPONDER AND EXAMPLES OF USE

CROSS REFERENCE TO RELATED APPLICATIONS

This application is a 35 USC 371 US National Stage filing based on International Application Serial No. PCT/IB2005/ 003922, which claims priority to U.S. Provisional Application Ser. No. 60/639,235 entitled METAL ENCASED PASSIVE RADIO FREQUENCY TRANSPONDER AND MATERIAL TRACKING SYSTEM, filed Dec. 22, 2004 and Ser. No. 60/669,953, entitled INTELLIGENT IMPLEMENT HAVING READABLE ELEMENT PROVIDING PRECISE SIZE INFORMATION TO IMPROVE SURGICAL ACCURACY, filed Apr. 8, 2005, the contents of which are incorporated herein by reference thereto.

BACKGROUND OF THE INVENTION

This invention relates to operative, computer assisted surgical implements and related systems, and more particularly, to implements and corresponding systems which include radio frequency identification transponders encased in intelligent instruments used at the operative site.

The need for such encased RFID transponders is known from German Patent application DE10239710A1. However, such references do not describe a functioning means of encasing the transponder in metal.

Further, the inventory management of expensive and mission-critical tools may be enhanced through the use of RFID transponders affixed to an implement.

Sterilization of implements subjects the instrument to a harsh environment which can damage an RFID transponder.

Further, there is a perceived fear that any plastic encasing material can eventually be broken down in a typical sterilization environment such as in an auto-clave.

Still further, computer assisted navigational surgery can be improved when precise geometric or dimensional information is stored in and retrievable from a surgical implement. Currently, precision is increased at considerable cost, as more precise machining methods are required to attain the higher and higher precision implements.

A need therefore exists for an implement and a system which is capable of hermetically encasing an RFID transponder in metal, so as to better protect the transponder from harsh sterilization environments. Further, a need exists for a system and implement for use in the system that improves inventory management of expensive and mission-critical equipment and which also may facilitate use of low precision-manufactured instruments to nonetheless attain a highly precise result.

SUMMARY OF THE INVENTION

A metal-encased passive radio-frequency transponder assembly (10, 110, 110') includes a metal housing (20, 112, 112') having an external surface (22) and an opening (24) accessing an interior space (30), the opening closeable with a metal cover (28) to provide a solid metal encasement (14). The interior space (30) of the encasement is defined by the interior walls of the housing and cover. The solid metal encasement has a substantially uniform wall thickness (T) between the interior wall surface adjacent which an antenna assembly (70) is disposed and the opposing external surface (22) of less than about 0.5 mm. A passive radio-frequency transponder device (124, 124') is received within the interior space (30) of the housing (20, 112, 112'). The passive transponder device (124, 124') has an iron core antenna assembly (50). The antenna assembly (50) is disposed adjacent the interior wall surface of the interior space and oriented to maximally couple a radio-frequency signal present at the interior wall surface to an antenna (70) of the antenna assembly (50).

BRIEF DESCRIPTION OF THE DRAWINGS

FIGS. 6A and 6B are specification sheets for transponder units practicable in the present metal-encased, passive RF transponder device.

FIG. 6C is a schematic drawing of the test device used to elucidate the electro-physical parameters of the present metal-encased, passive RF transponder device.

FIG. 7A is a cross-sectional view of a housing showing the cover plate sealed in place and a passive transceiver device disposed in proper orientation within the housing for maximum RF signal coupling to the antenna of the device.

FIG. 7B is a cross-sectional view of a housing showing the cover plate sealed in place and a passive transceiver device disposed in proper orientation within the housing as in FIG. 7A.

FIG. 12A is a side view of a second implement of the invention.

FIG. 12B is a bottom view of the second implement of the invention.

DETAILED DESCRIPTION OF THE PREFERRED EMBODIMENT(S)

Figure 2:
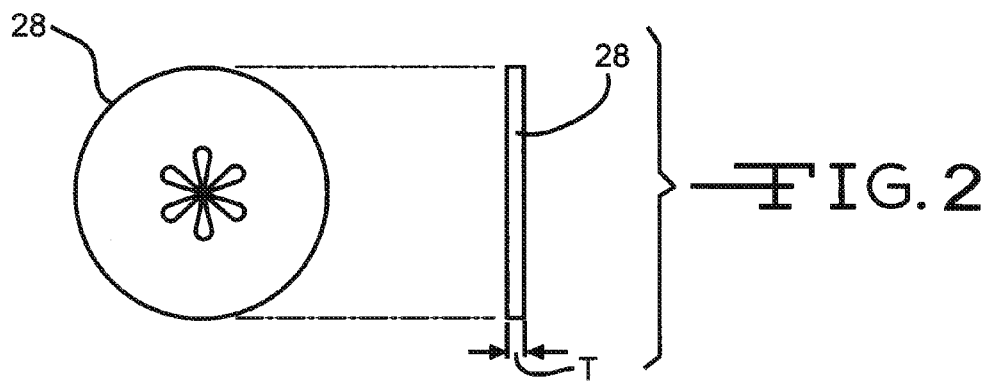
FIGS. 1A and 2 are perspective and plan views of a metal housing and metal cover plate for the present metal encased, passive radio-frequency transponder.

Referring now to the drawings, the details of preferred embodiments of the present invention are graphically and schematically illustrated. Like elements in the drawings are represented by like numbers, and any similar elements are represented by like numbers with a different lower case letter suffix.

Figure 1A:
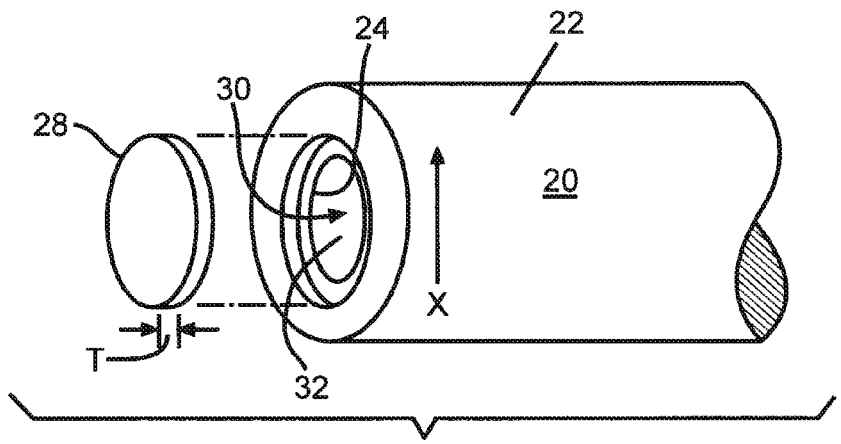
Figure 10:
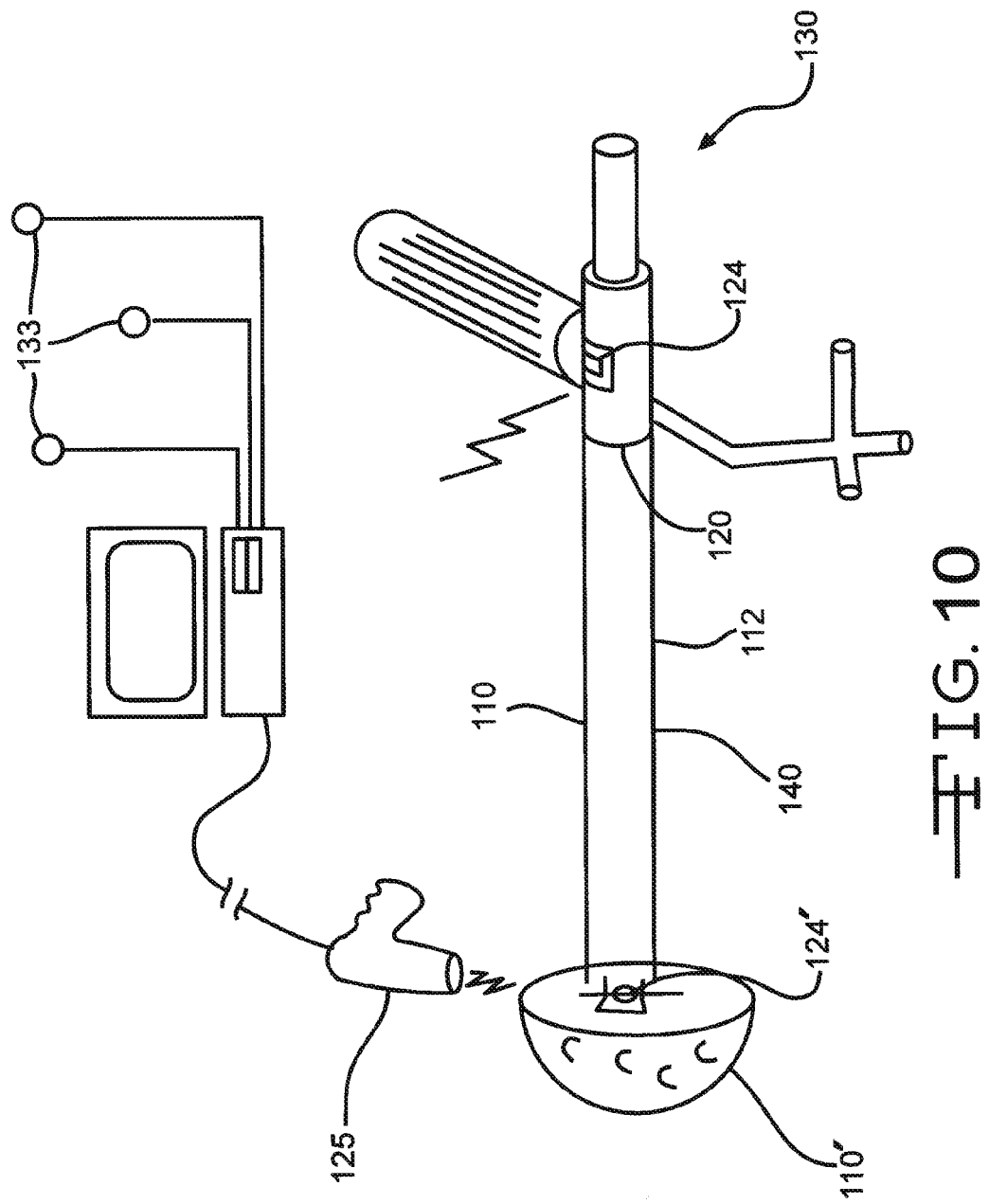
FIG. 10 is a perspective view of an alternate system of the invention.
Figure 11:
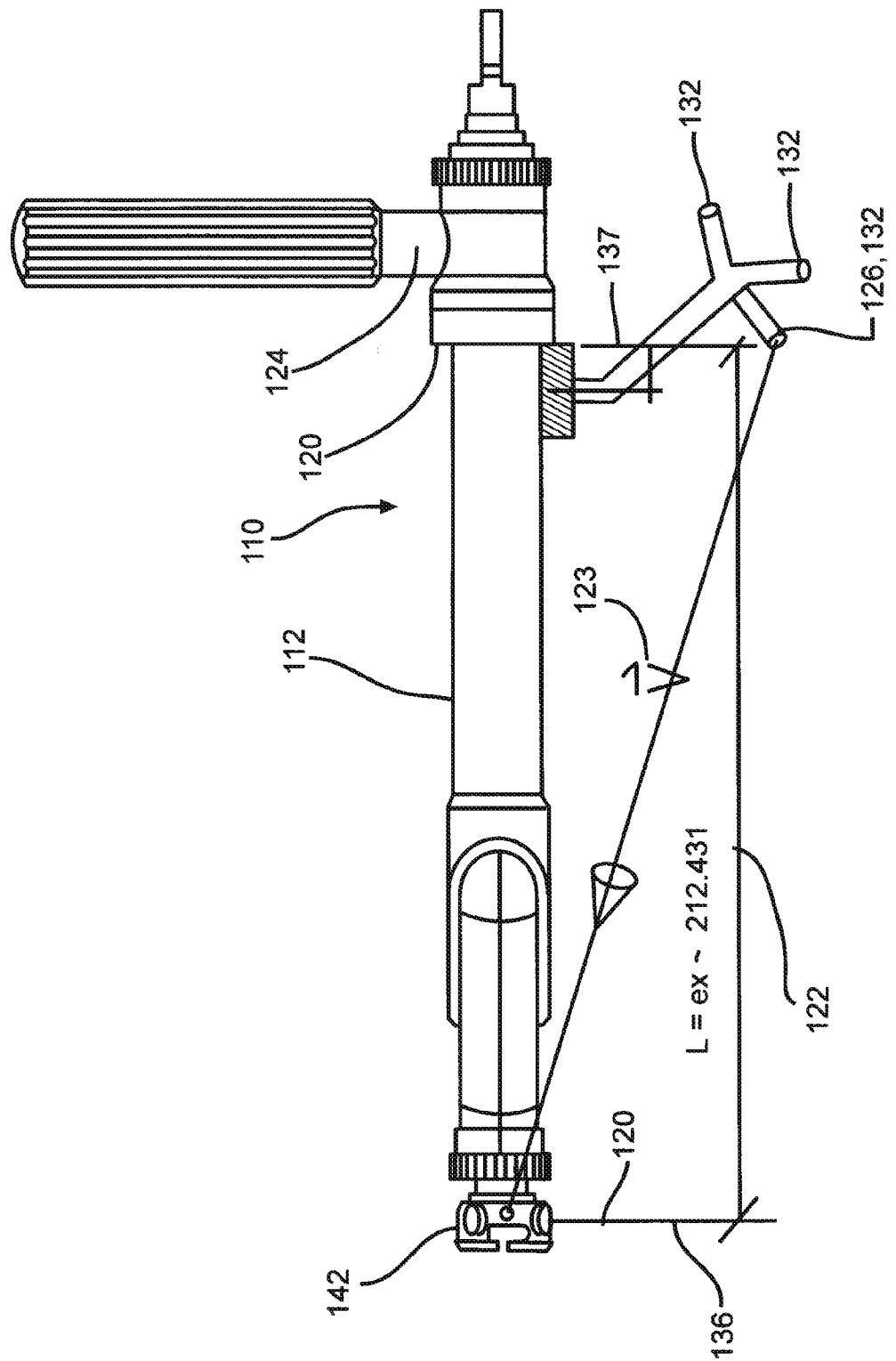
FIG. 11 is a top view of an implement of the invention.

Referring now to FIGS. 1A and 2, a metal housing 20 and metal cover plate 28 encases the passive radio-frequency transponder 124 (FIGS. 10 and 11). In this embodiment, the axis of the antenna 70 is perpendicular to the critical thickness of the cover plate 28.

The present invention encompasses a fully metal-encased passive radio-frequency transponder device and its exemplary uses. The transponder device is fully metal-encased in that the encasement or jacket of the transponder device has no non-metallic gaps, spaces, cracks, pores or the like. In other words, it is an important feature of the present invention that encasement has a continuous metal surface. The present metal-encased transponder device is the basic tracking unit of a materiel tracking system, wherein implements to be tracked, especially metallic items include an embedded or affixed transponder device of the present invention.

Figure 1B:
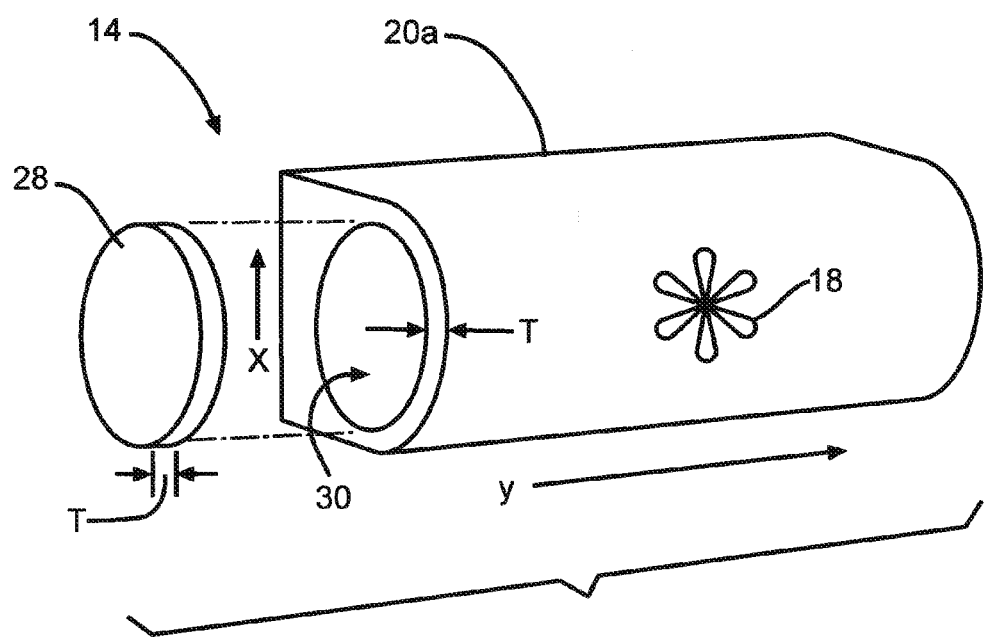
FIG. 1B is an alternative encasement having the capability to be read in two dimensions, x and y.

Referring now to FIG. 1B, an alternative encasement has the capability to be read in two dimensions, x and y. Additionally, this embodiment of the present metal-encased, passive radio-frequency transponder is intended to be fixed to the implements to be tracked rather than having the housing 20a be integral to the item.

Figure 3:
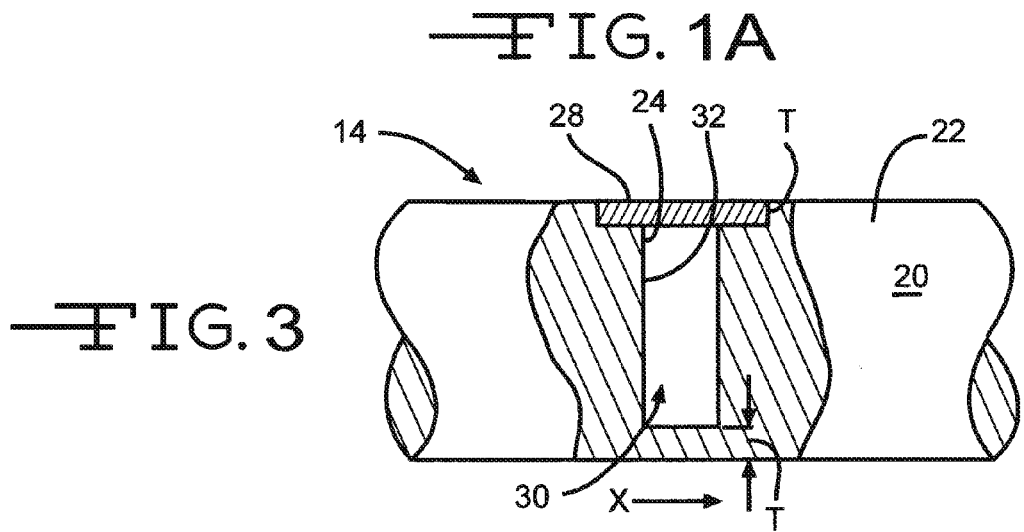
FIG. 3 is a partial cross-sectional side view drawing illustrating an alternative orientation of the interior space of the housing for within a rod-type encasement.

Referring now to FIG. 3, an alternative orientation of the interior space of the housing 20 is suitable for encasement within a rod-shaped encasement. Note that on placement of the transponder device in the housing 20, the antenna 70 maintains a perpendicular orientation to the critical thickness of the encasement, i.e. the cover plate 28. Additionally, in this embodiment, there is a second point of critical thickness at the bottom end of the interior space of the housing 20.

Figure 4B:
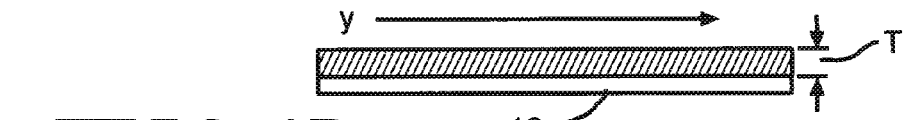
FIG. 4B is a cross-sectional side view of the arcuate cover plate having the critical thickness for the encasement of FIG. 4A.
Figure 4A:
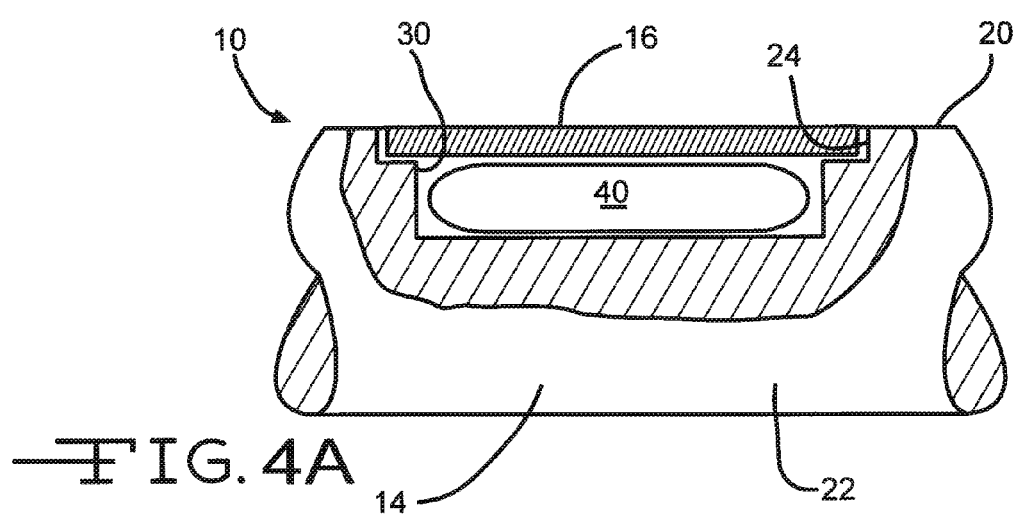
FIG. 4A is a partial cross-sectional side view drawing of an encasement illustrating a housing and cover plate configuration allowing signal coupling with the antenna in a dimension 90° from that of FIGS. 1A, 1B and 3.
Figure 4C:
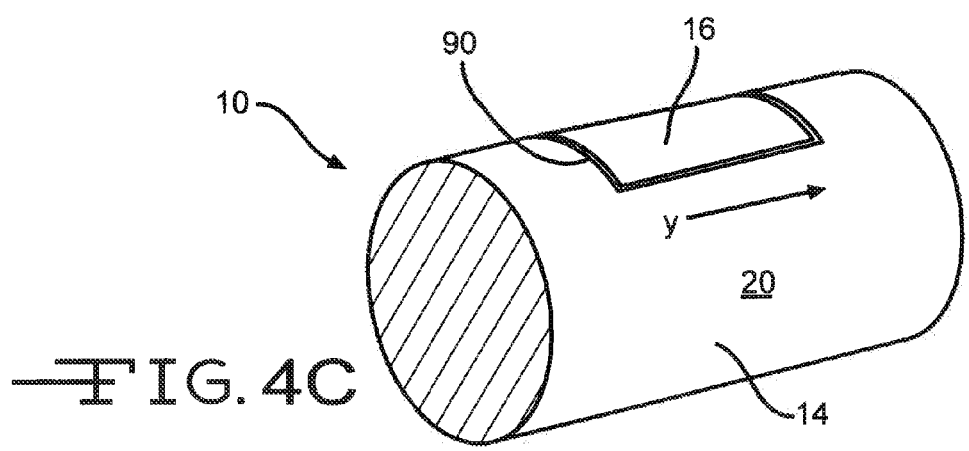
FIG. 4C is a perspective view of a rod portion of the encasement of FIG. 4A showing the cover plate fixed in place over the opening of the housing.

Referring now to FIG. 4A-4C, an encasement 14 illustrating a housing and cover plate configuration is shown wherein placement of the transponder unit is such that the axis of its antenna is parallel to the critical thickness of the encasement. This allows signal coupling with the antenna in a dimension 90° from that of FIGS. 1 and 3. As shown in FIG. 4B, an arcuate cover plate 16 of critical thickness encases the RFID device of FIG. 4A.

Referring now to FIG. 4C, the cover plate 16 on a rod portion is fixed in place over the opening of the housing 20. The fully metal-encased passive radio-frequency transponder device 10 of the present invention thus includes a metal housing 20 having an external surface 22, and an opening 24 allowing access to an interior space 30 within the housing 20. The opening 24 is closable with a metal cover 16. The metal cover 16 is fixed to the housing 20 with a metallic seal 90 (e.g. welded or soldered) so that the combined housing 20 and cover 16 provide a solid metal encasement 14, with no non-metal gaps, cracks, spaces, pores or the like. This is particularly important in applications where a metal implement being tracked may be subject to conditions that the transponder unit 40 was not designed to be proof against.

The interior space 30 of the encasement 14 is defined by the interior walls of the housing 20 and cover plate 16. The solid metal encasement 14 (the encasement being the combination of the housing 20 and the cover plate 16) has at least one section of its wall that is substantially a uniform thickness T between an interior wall surface 32, adjacent which the antenna 70 of the transponder unit 40 is disposed. The thickness T, between an interior wall surface 32 and the opposing external surface 22, was less than about 0.5 mm. See Example 1.

Example 1

Reading Passive RF Transponders through a Fully Sealed Metal Encasement

Objectives
Feasibility Determination: is it possible to read a passive RF transponder device through solid metal.
Elucidate a set of electro-physical parametric limits for the capability to read a passive RF transponder device through solid metal.
Transponder design features
Thickness of the metal encasement
Read distance and orientation of the read unit to the antenna of the transponder.

Figure 6D:
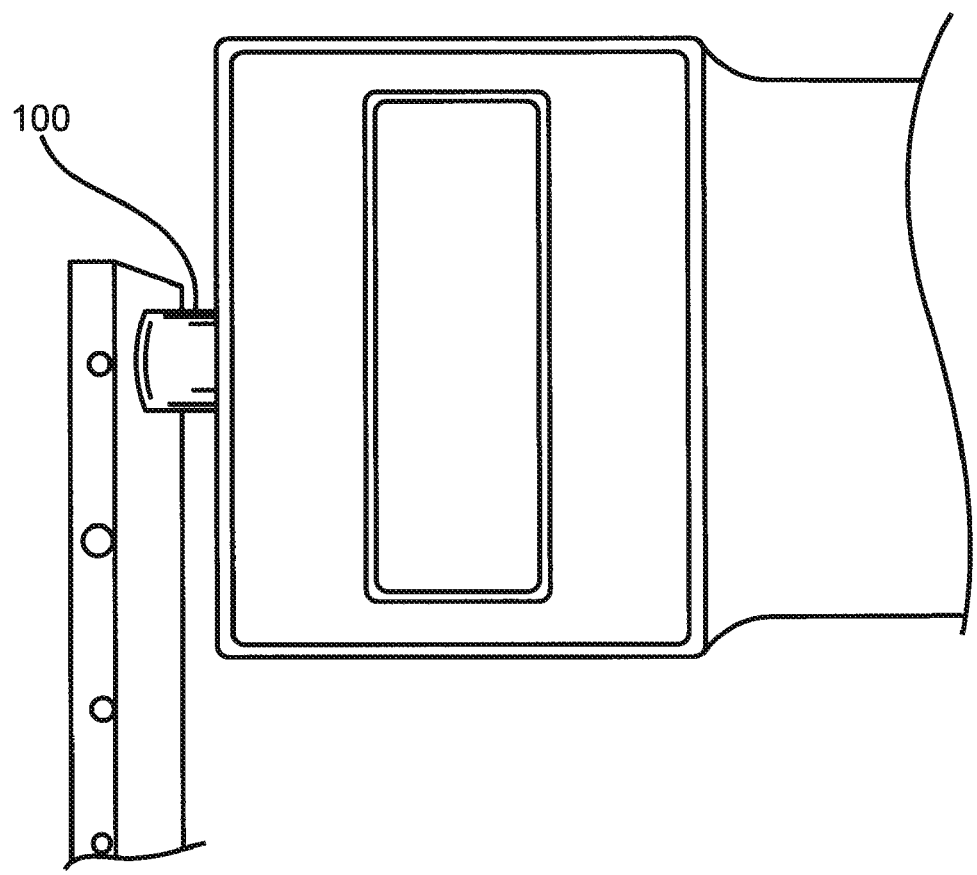
FIG. 6D illustrates one of two positional relationships between the metal-encased, passive RF transponder device and the read head of the reader.

Materials
601201 Sokymat GLASS TAG UNIQUE 2.12×12.0 Read Only 64 bit (FIG. 6A)
601203 Sokymat GLASS TAG UNIQUE 3.15×13.3 Read Only 64 bit (FIG. 6B)
Test Plate C6335 (FIG. 6C)
Reader: RFID tag reader with Ferrite Antenna (FIG. 6D)

Methods
A test plate C6335 was manufactured from 17-4 Stainless Steel, which is an alloy common in orthopaedic instrumentation. Both 12 mm (ITM# 601201) and 13 mm (ITM# 601203) read only Glass Unique tags were imbedded into holes drilled in the plate at varying depths of 0.3 mm, 0.4 mm and 0.5 mm. Every other hole was closed with a metallic plug which was subsequently laser-welded into the plate to encapsulate the tag inside. The remaining holes were left open as a control. The Easy Term battery powered reader was then placed adjacent to the side of the plate and prompted to read the RFID tags. In each case the control tag was read first and then the encapsulated tag was read. Exhibit D shows the test setup with the reader in place over an encapsulated RFID tag.

Results
All of the control tags 12 mm (ITM# 601201) and 13 mm (ITM# 601203) that were imbedded in open holes read successfully in the 0.3 mm, 0.4 mm and 0.5 mm thickness. Both the 12 mm (ITM# 601201) and 13 mm (ITM# 601203) tag that were completely encapsulated in the metal read through the 0.3 mm and 0.4 mm, however both were unsuccessful at 0.5 mm.

Conclusion and Discussion
It is clear that as long as there is an opening in the metal housing 20 either tag could be read successfully no matter what the depth. When the tags were encapsulated the read distance was diminished but still easily readable at the 0.3 mm and 0.4 mm thickness. The manufacturer hypothesizes that ferrite material present in their tags and ferrite in the reader contributes to focus the signal into a tight pattern so that it can be read through metal. They believe that the ferrite material creates an alignment of the magnetic fields that attract one another, the reader pushing the signal and the tag pulling it in. Further they hypothesize that as long as the reader has a sufficiently strong ferrite core in its antennae the ferrite in the tag could be removed. Also it is hypothesized that standards tags (e.g., Sokymat's) could be encapsulated in metal and written to. Further testing will be required to prove the theory of reading tags without ferrite cored and writing to their chips through metal.

Summary of a Working Parameter Set
- A passive transponder device having an iron core and wound antenna
- Less than 0.5 mm thickness of metal between the reader device and the transponder device.
- An aspect angle of the read unit head to the antenna axis of substantial 0° or 90°.

Figure 5:
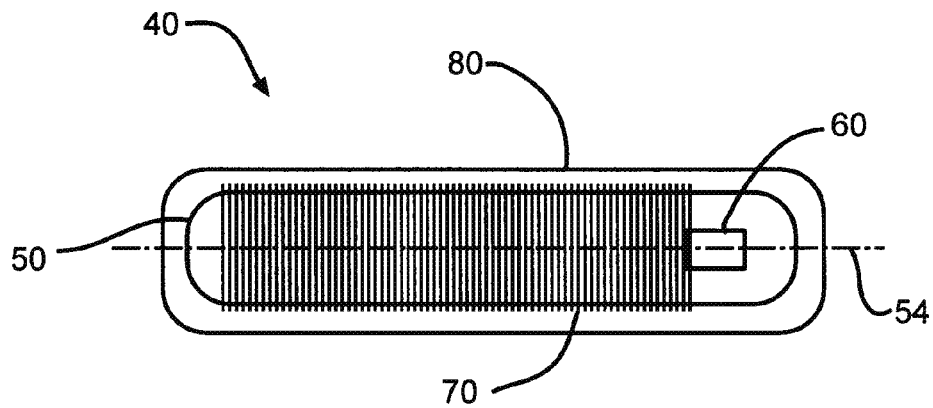
FIG. 5 is a schematic representation of the parts layout of a passive transceiver device appropriate for practice in the present invention.

Having determined at least one working set of electrophysical parameters the present solid metal-encased passive radio-frequency transponder device 10 is enabled and practicable in a metal encasement in the following manner. As generally illustrated in FIG. 5, in the preferred embodiment, a passive transponder 40 having an iron (ferrite) core antenna assembly 50 was used (part no. 601201: GLASS TAG UNIQUE 2.12×12.0 Read Only 64 bit and part no. 601203: GLASS TAG UNIQUE 3.15×13.3 Read Only 64 bit; Sokymat S. A., Switzerland). The transponder 40 was received within the interior space 30 of the encasement 14.

Referring now to FIGS. 6A and 6B, specification sheets for transponder units which are practicable in the present metal-encased, passive RF transponder device are shown. FIG. 6C illustrates a test set up device used to elucidate the electro-physical parameters of the present metal-encased, passive RF transponder. FIG. 6D illustrates one of the positional relationships between the metal-encased, passive RF transponder test device of FIG. 6C and the read 100 head of a "reader" as used to used to elucidate the electro-physical parameters.

FIG. 7A is cross-sectional view of a housing 20 showing the cover plate 28 sealed in place and a passive transceiver device 40 disposed in proper orientation within the housing 20 for maximum RF signal coupling to the antenna of the device. In FIG. 7B, a housing 20 is shown with its cover plate 28 sealed in place and a passive transceiver device 40 disposed in proper orientation within the housing 20 as in FIG. 7A, but additionally illustrating the signal relationship between the iron core antenna 70 and a signal source outside (read head 100) and the housing 20.

It was determined that the orientation of the antenna 70 relative to the read device head 100 (see FIGS. 6D and 7B) was important. That is, the dimensional or orientation aspect x or y of the antenna 70 relative to the critical thickness T portion of the encasement 14 was enabling when the axis 54 of the antenna 70 was either substantially perpendicular to or parallel with the plane of the critical thickness T portion. Specifically, the antenna 70 was disposed adjacent the interior wall surface 32 of the interior space 30 and oriented to maximally couple a radio-frequency signal present at the interior wall surface to an antenna of the antenna assembly when the axis 54 of the antenna was substantially perpendicular to (the x dimension, see FIG. 3) or parallel with (the y dimension, see FIG. 4C) the plane of the critical thickness T portion of the encasement 14. As illustrated in FIGS. 1B and 3, the encasement 14 of the present transponder device 10 can be configured to have more than one critical thickness T portion, and thus be read from more than one antenna dimensional aspect x or y. Other configurations of the encasement 14 are selectable by one of ordinary skill in the art in consideration of the configuration of the implement it is to be incorporated into, and in view of the teachings and drawings disclosed herein. It may be useful in certain applications to scribe an optional orientation mark 18 on the encasement to make readily apparent the optimal location for activating the transponder device 10 with a reader.

In a preferred embodiment, the materiel radio-tracking and inventory system of the present invention has a tertiary organizational structure. At the first level of organization, a metallic implement to be tracked incorporates or has fixed to it the present metal-encased, passive RF transponder device 10 described above. The present metal-encased, transponder device 10 is the first passive radio-frequency transponder in the system hierarchy. The transponder device 10 of the preferred embodiments disclosed herein was a read-only device. Once it was loaded with its response data, the data could not be changed by an external signal. The read-only device has advantages in a material tracking system, in that the code cannot be changed in the field, and the change used to avoid tracking of a more restricted item masking as a less restricted one. However, it is intended that the transponder device 10 include both read-only and read-write types of transponder units 40.

Figure 8A:
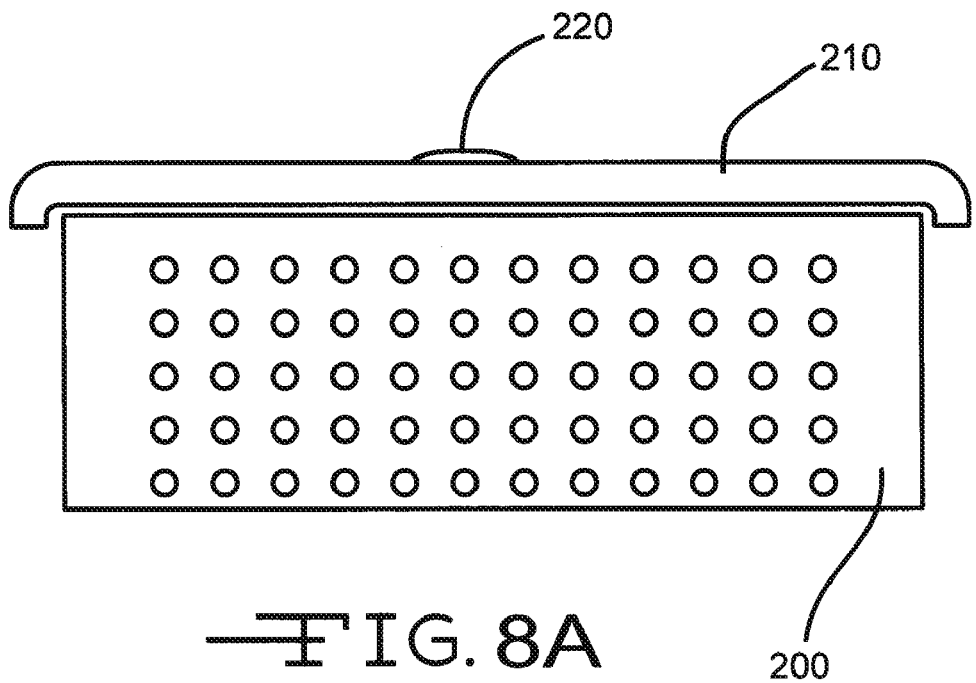
FIG. 8A is a side view of a typical storage bin used in hospitals and such for containing medical instruments and supplies.

Referring now to FIG. 8A, a typical storage bin is typically used in hospitals for containing medical instruments and supplies. A non-encased passive transceiver is attached to an external surface of the bin—the top, in this case.

Methods and procedures for entering an implement into the tracking system are known in the art. Typically, the transponder device 10 is powered up, and its identification coding is read from memory and transmitted when activated by an appropriate reader transceiver device. At other appropriate times, as when the status of the item is changed, the transponder device 10 is read again in conjunction with the status update. It is anticipated that the implement will be kept in a storage unit 200, such as a container or bin (FIG. 8A). The storage unit 200 is configured to receive and store at least one implement to be tracked. The storage unit 200 has a surface 210 on which a second passive radio-frequency transponder 220 is mounted. The second transponder 220 can be mounted on an internal surface or an external surface.

Figure 8B:
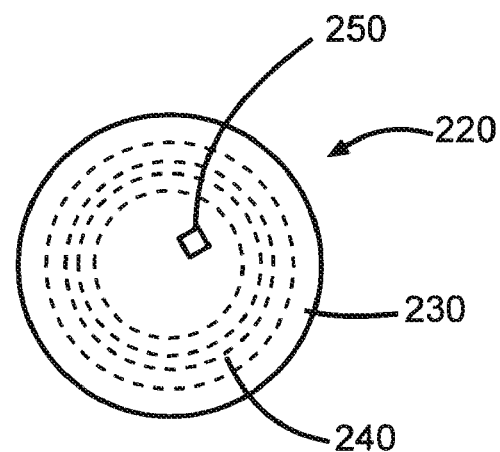
FIG. 8B is a top view schematic representation of the non-encased passive transceiver device.

Referring now to FIG. 8B, a non-encased passive transceiver device of a preferred embodiment is shown. The second transponder 220 does not have a solid metal encasement. This is not necessary if the storage unit 200 is not metal or RF shielded. It is encapsulated in a housing 230, in resin of the preferred embodiment illustrated, and does have the antenna 240 and electronics 250 typical of such devices. The second passive RF transponder 220 is a read-write device, and is disposed to power up, receive and write data to memory, and to read and transmit data from memory as appropriate when activated by a read/write transceiver device. The data stored or storable on the second transponder device 220 includes the storage unit identification code and the identification code of the implement to be tracked that is stored in the unit 200.

Figure 9:
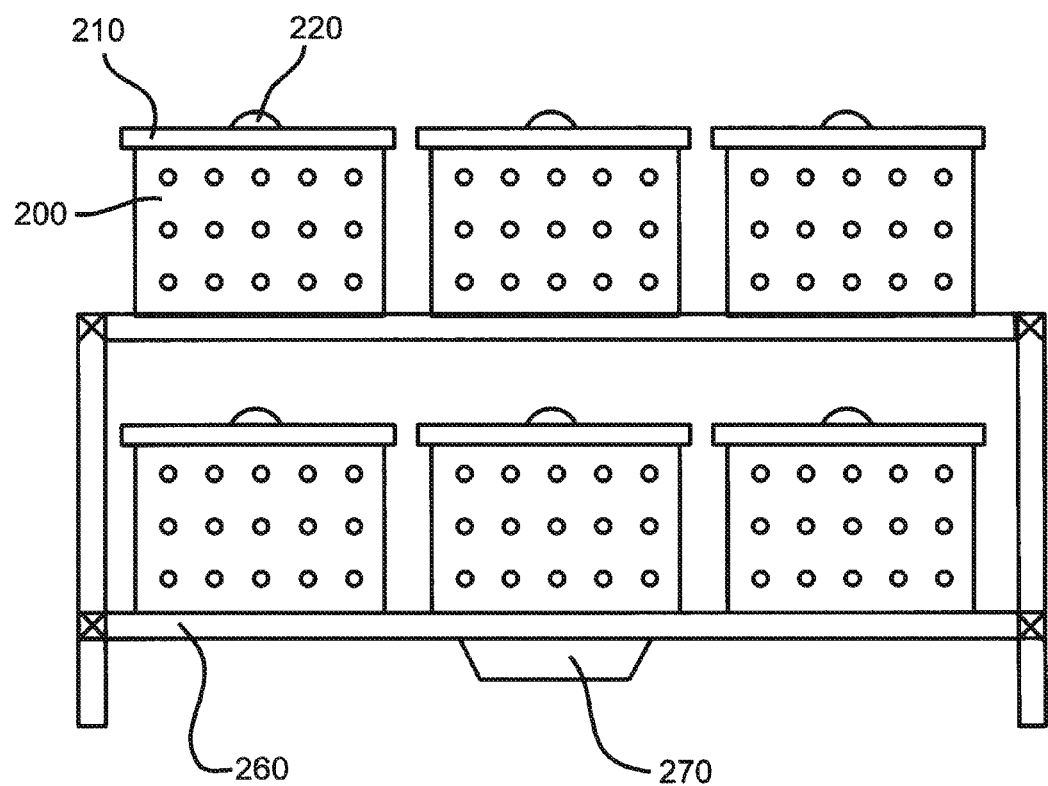
FIG. 9 is a side view illustration of a typical bin rack used in hospitals and the like to hold storage bins.

Referring now to FIG. 9, a typical bin rack typically used in hospitals holds storage bins. The rack has an active transceiver device mounted on it. The storage rack 260 is configured to hold the storage units 200 in a manner to expose the second passive radio-frequency transponder 220 to be activated by a read/write. However, this configuration of the storage rack 260 may readily be changed to accommodate other desired features, such as not having the second transponders 220 exposed. Additionally, the storage rack 260 has an active radio-frequency transponder 270 mounted on it. The active transponder 270 is disposed to receive and write data to memory, and to read and transmit data from memory as appropriate when activated. Activation of the active transponder 270 can be manual or automatic, and remote or local. In certain applications where it might be expected that a transportable rack 260 may move considerable distances (or to avoid it moving considerable distances) the active transponder may include a locator device (e.g. a GPS device). The read-write and read-only data processable by the active transponder 270 may include a storage rack identification code and the identification code of the storage units held in the rack, as well as location data. Taken in combination, these elements alone and in various combinations comprise the metal encased passive radio frequency transponder and materiel tracking system of the present invention.

Further Examples of Use

Referring to FIGS. 10, 11, 12A, and 12B, in another example of use, an intelligent implement 110, 110' for surgical use has an implement body 112, 112', an RFID transponder 124, 124' according to the invention, and a reference device 126, 126'. The implement body 112, 112' has a structure having features 120, 120' of precise dimensional characteristics 122, 122'. The RFID transponder 124, 124' is encased in the body 112, 112', and is capable of storing information about select precise dimensional characteristics 122, 122' of the body. The reference device 126, 126' is defined on the implement, from which the dimensional characteristics are referenced for use in a computer-aided navigation system 130. The reference device 126 is preferably a navigational sputnik affixed to the body 112. The sputnik 126 has features 132 which enable the navigation system 130 to know the precise orientation of the implement in three dimensional space.

In the implement 110, the sputnik or satellite 126, includes a plurality of spatial reflectors 132 whose location is readable by a position sensing device (e.g. multiple, spatially displaced, infrared detectors 133, radar, GPS, etc) of the navigation system 130 connected to a computer of the navigation system 130 and, given that the plurality of spatial reflectors 132 are located a known vector distance 134 away from a reference plane 136, 137, 136', 137', then the location of this reference plane can be accurately ascertained.

The spatial reflectors 132 are infrared reflectors.

The reference plane is a tool attachment plane 136.

In a preferred embodiment, the implement 110, 110' is adapted for connecting with a second intelligent implement 110', 110, the two together creating a compound intelligent implement 140. An appropriate attachment means may be a bayonet mechanism, such as that shown in WO 03/092513 (PCT/IB03/01725), the content of which is incorporated herein by reference thereto.

The second implement 110' is a tool which connects to a reference interface 142 located a known distance away from a reference plane 136, 137, the corresponding RFID transponder 124, 124' being adapted to store the known distance value 122, 122'.

The RFID transponder 124, 124' is a readable RFID chip; a readable, writable RFID chip, readable; and/or writable by a reader 125.

The RFID transponder 124, 124' is embedded or encased in the implement.

The RFID transponder 124, 124' may be embedded or encased in the implement under a thin metal cover 125.

In another embodiment, the invention is included in an implement which is one of a lot of intelligent implements 110, 110' for use in holding a tool 110 to be used in computer assisted navigation system 130, each implement having an implement body 112, 112' made according to manufacturing processes that reproduce dimensional characteristics which vary amongst themselves within a tolerance band, wherein, in order to provide greater accuracy during computer assisted surgery, prior to delivery to the point of use, each implement 110, 110' is measured for its particular precise dimensional reference characteristic 122, 123, 122', 123' and such dimensional characteristic is recorded via an RFID transponder 124, 124' and affixed thereto, so as to be able to be read and input into a register of a computer conducting computer aided navigational surgery therewith, thus providing the computer with more accurate tool position information.

The dimensional reference characteristic 123' is the vector distance between a navigational sputnik 126 affixed to the implement and a reference plane 136 of the tool engaging portion 142 of the implement.

An object of the invention is to provide an implement and a system which is capable of hermetically encasing an RFID transponder in metal, so as to better protect the transponder from harsh sterilization environments.

Another object of the invention is to provide an implement and a system that improves inventory management of expensive and mission-critical equipment.

Another object of the invention is to enable the manufacturing of implements using conventional and relatively inexpensive means, while assuring precision when such implements are used in computer assisted navigational surgery.

Multiple variations and modifications are possible in the embodiments of the invention described here. Although certain illustrative embodiments of the invention have been shown and described here, a wide range of modifications, changes, and substitutions is contemplated in the foregoing disclosure. In some instances, some features of the present invention may be employed without a corresponding use of the other features. Accordingly, it is appropriate that the foregoing description be construed broadly and understood as being given by way of illustration and example only, the spirit and scope of the invention being limited only by the appended claims.

What is claimed is:

1. An intelligent implement for surgical use, the implement comprising:
   a) an implement body;
   b) a metal housing having an external surface provided with an opening accessing an interior space thereof, wherein the opening in the housing is closable with a metal cover to provide an encasement having a substantially uniform wall thickness (T) of less than 0.5 mm measured from an interior wall surface to the external surface;
   c) a passive radio-frequency transponder comprising an iron core antenna received within the interior space of the encasement and oriented to effectively couple a radio-frequency signal present at the interior wall surface to the antenna, wherein the encasement including the passive radio-frequency transponder and antenna is in at least a metal portion of the implement body; and
   d) a reference device defined on the implement body, wherein the transponder stores information about select dimensional characteristics referenced on the implement body with respect to the reference device, the dimensional characteristics being usable in a computer-aided navigation system.

2. The implement of claim 1 wherein the reference device is a navigational sputnik affixed to the body, the sputnik having features which enable the navigation system to know the precise orientation of the implement in three dimensional space.

3. The implement of claim 2 wherein sputnik comprises a plurality of spatial reflectors whose location is readable by a position sensing device of the navigation system connected to a computer of the navigation system and, given that the plurality of spatial reflectors are located a known vector distance away from a reference plane, then the location of this reference plane can be accurately ascertained.

4. The implement of claim 2 wherein the position sensing device comprises a plurality of spatially displaced infrared detectors.

5. The implement claim 3 wherein the position sensing device is a radar.

6. The implement of claim 3 wherein the position sensing device is a GPS.

7. The implement of claim 3 wherein the spatial reflectors are infrared reflectors.

8. The implement of claim 3 wherein the reference plane is a tool attachment plane.

9. The implement of claim 1 adapted for connecting with a second intelligent implement, the two together creating a compound intelligent implement.

10. The implement of claim 9 wherein the second implement comprising an RFID transponder is a tool which connects to a reference interface located a known distance away from a reference plane, the corresponding RFID transponder being adapted to store the known distance value.

11. The implement of claim 1 wherein the RFID transponder is a readable RFID chip, readable by a reader.

12. The implement of claim 1 wherein the RFID transponder is a readable, writable RFID chip, readable and writable by a reader.

13. The implement of claim 1 wherein the RFID transponder is embedded or encased in the implement under the metal cover.

* * * * *